United States Patent
Rzasa et al.

(10) Patent No.: US 6,771,369 B2
(45) Date of Patent: Aug. 3, 2004

(54) SYSTEM AND METHOD FOR PHARMACY VALIDATION AND INSPECTION

(75) Inventors: David M. Rzasa, Boulder, CO (US); Robert J. Faus, Longmont, CO (US); Brian Curtiss, Boulder, CO (US); Alexander F. H. Goetz, Boulder, CO (US); John Enterline, Boulder, CO (US)

(73) Assignee: Analytical Spectral Devices, Inc., Boulder, CO (US)

(*) Notice: Subject to any disclaimer, the term of this patent is extended or adjusted under 35 U.S.C. 154(b) by 142 days.

(21) Appl. No.: 10/097,530

(22) Filed: Mar. 12, 2002

(65) Prior Publication Data

US 2003/0174326 A1 Sep. 18, 2003

(51) Int. Cl.⁷ .............................. G01J 3/42; G01N 21/33
(52) U.S. Cl. ................. 356/326; 356/328; 250/339.07; 250/372
(58) Field of Search ................................ 356/326, 328; 250/339.07

(56) References Cited

U.S. PATENT DOCUMENTS

| | | |
|---|---|---|
| 4,143,770 A | 3/1979 | Grimmell et al. |
| 4,183,013 A | 1/1980 | Agrawala et al. |
| 4,573,606 A | 3/1986 | Lewis et al. |
| 4,640,560 A | 2/1987 | Blum |
| 4,918,604 A | 4/1990 | Baum |
| 4,991,223 A | 2/1991 | Bradley |
| 5,337,919 A | 8/1994 | Spaulding et al. |
| 5,441,165 A | 8/1995 | Kemp et al. |
| 5,490,610 A | 2/1996 | Pearson |
| 5,502,944 A | 4/1996 | Kraft et al. |
| 5,522,512 A | 6/1996 | Archer et al. |
| 5,562,232 A | 10/1996 | Pearson |
| 5,597,995 A | 1/1997 | Williams et al. |
| 5,660,305 A | 8/1997 | Lasher et al. |
| 5,679,954 A | 10/1997 | Soloman |
| 5,712,658 A | 1/1998 | Arita et al. |
| 5,713,487 A * | 2/1998 | Coughlin ........................ 221/2 |
| 5,720,154 A | 2/1998 | Lasher et al. |
| 5,771,657 A | 6/1998 | Lasher et al. |
| 5,900,634 A | 5/1999 | Soloman |
| 5,915,560 A | 6/1999 | George et al. |
| 6,014,631 A | 1/2000 | Teagarden et al. |
| 6,176,392 B1 | 1/2001 | William et al. |
| 6,202,923 B1 | 3/2001 | Boyer et al. |
| 6,356,873 B1 | 3/2002 | Teagarden et al. |
| 6,535,637 B1 | 3/2003 | Wootton et al. |

FOREIGN PATENT DOCUMENTS

EP    0 887 638 A1    12/1998

* cited by examiner

Primary Examiner—F. L. Evans
(74) Attorney, Agent, or Firm—Cooley Godward LLP

(57) ABSTRACT

An apparatus for verifying the identity of a dispensed pharmaceutical comprises an analysis unit adapted to determine a property of the dispensed pharmaceutical, an input device adapted to receive predetermined identifying information corresponding to the dispensed pharmaceutical, and a comparison unit adapted to compare the determined property of the dispensed pharmaceutical with the predetermined identifying information. In addition, a method of verifying a prescription, wherein the prescription comprises a pharmaceutical compound, comprises associating the prescription with a unique identifier, storing the unique identifier, determining the identity of the pharmaceutical compound, and comparing the identity of the pharmaceutical compound with the unique identifier.

12 Claims, 7 Drawing Sheets

SYSTEM AND METHOD FOR PHARMACY VALIDATION AND INSPECTION

FIELD OF THE INVENTION

The present invention pertains to spectrometer and reflectance data analysis and more particularly to the validation and identification of packaged pharmaceuticals in a retail setting.

BACKGROUND OF THE INVENTION

There is an ongoing and predicted long-term shortage of licensed pharmacists. Due to the increasing age of the population and the ever-increasing number of prescription medicines available, the demand for prescription drugs is growing at rate that will far exceed the capacity and numbers of licensed pharmacists. According to the National Association of Chain Drug Stores, the number of prescriptions filled between 2000 and 2005 will increase by 41%, while the number of retail pharmacists will only increase by 4.5%. The net impact of this imbalance is that pharmacists are increasingly spending more time doing clerical and administrative tasks such as verifying filled prescriptions and checking data entry done by pharmacy technicians. Since the capacity of any one pharmacist is fixed, the output of a pharmacy has become constrained. Consequently, the labor and total cost per prescription continues to rise. The December 2000 Department of Health and Human Services Report to Congress titled "The Pharmacist Workforce: A Study of the Supply and Demand for Pharmacists", which is hereby incorporated by reference into the present application, provides an overview of the above problem.

Due to these increased demands on a pharmacist's time, and the resulting increased reliance on technicians and other non-professional staff to fill prescriptions, there is an increased chance for prescription error. While these errors may take many forms, the likelihood of a dangerous or life threatening "adverse drug event" increases proportionally with the increased chance of prescription fill error. Several studies have shown that prescription error rates are consistently in the 2% to 7% range, with a 4% error rate often cited as a reliable average. The number of deaths due to medication errors is estimated to exceed 7000 per year in the United States alone. This number does not include non-fatal conditions from drugs that also result in some form of trauma or injury. The resulting litigation costs associated with these prescription fill errors has also dramatically increased. Available information shows that settlements from such lawsuits average $500,000 per incident. A known study on this subject is the 1999 Institute of Medicine Report: "To Err is Human: Building a Safer Heath System", the details of which are hereby incorporated by reference into the present application.

Existing pharmacy filling systems and procedures still require a human operator, whether that operator is a technician or a licensed pharmacist, to validate visually whether the drug that is delivered to the customer is correct. Thus, the human factor contributes to the majority of prescription fill errors. Existing visual verification techniques rely on comparing an electronic image of the prescribed medication, i.e. a picture of the prescribed medication retrieved from a data library, with the actual medication that is dispensed for the patient. Other systems and procedures rely on comparing the dispensed medication with that in the original manufacturer's supply container, or comparing an electronic image of the filled prescription with an electronic image of the prescribed medication retrieved from a data library. Each of these existing verification systems present similar problems.

First, these known verification methods assume that all drugs are visually distinct. This assumption causes many problems because many drugs are not, in fact, visually distinct and, in other cases, the visual differences between drugs is very subtle. For instance, manufacturers are rapidly running out of unique shapes, colors and sizes for their solid dosage form products. To further complicate the problem, generic drug manufactures are using shapes, colors, and sizes that are different than that of the original manufacturer.

Second, even though some known systems may utilize a National Drug Code (NDC) bar code to verify that the supply bottle being accessed corresponds correctly to the patient's prescription, a fraction of filled prescriptions that are never picked up are returned to the supply shelves for reuse in later prescriptions. These reused bottles will not, therefore, have a manufacturer's bar code on them. It is, therefore, impossible to incorporate such validation schemes for these unused prescriptions. Furthermore, in these circumstances, a supply bottle is not available for a visual comparison with the filled prescription.

Finally, each of these known manual verification and validation techniques requires that the pharmacist spend a significant portion of his day performing these administrative or clerical tasks and allows less time for patient consultation and other professional pharmacist activities. This fact in itself is considered one of the leading reasons for the decline in graduation rate of professional pharmacists. The ability to allow the pharmacist to focus more on patient counseling rather than clerical and administrative duties is widely seen as an important promotional effort to meet the increasing demand for professionally trained pharmacists. Similarly, personal service by a pharmacist is cited in the 2001 Chain Pharmacy Industry Profile as one of the main reasons that a customer will choose any particular pharmacy.

Solid dosage pharmaceuticals (e.g. pills, tablets, and capsules) each have a unique chemical composition associated with them. This is often referred to as a chemical signature or fingerprint. Pharmaceuticals with varying dosage levels of the same active ingredient may have unique chemical signatures as well. Even slight variations in the active ingredient will produce a unique chemical signature. In that regard, most pharmaceuticals can be identified accurately by the use of some form of chemical analysis. This same methodology may be applied to other forms of medication (e.g. liquids, creams, and powders).

While there are many forms of chemical analysis, Near-Infrared (NIR) spectroscopy is one of the most rapidly growing methodologies in use for product analysis and quality control. For instance, NIR spectroscopy is being increasingly used as an inspection method during the packaging process of pharmaceuticals or food products. More and more often, this technique is augmenting or even replacing previously used vision inspection systems. For example, a system that utilizes a combined visible and NIR spectroscopy inspection system can be used to inspect a pharmaceutical product for, among other things, chemical composition, color, and dosage level.

Particularly with solid dosage pharmaceutical products, while a group or package of products may look identical in the visible portion of the spectrum each product may have a unique chemical signature in the near-infrared wavelength range (800–2500 nm). Details of packaging and inspection systems that utilize NIR as an inspection technique can be found in U.S. patent applications Ser. Nos. 10/023,302, 10/023,395, and 10/023,396 filed on Dec. 20, 2001 and U.S. patent application Ser. No. 10/068,623 filed on Feb. 5, 2002, the details of which are hereby incorporated by reference into the present application.

What is unique about these NIR spectrographic inspection and validation systems is the completely "hands-off" approach that can be utilized, and the reduced need for operator interaction in validating the composition of packaged and filled pharmaceuticals. What is needed, therefore, is a system that can utilize the unique chemical signatures of known pharmaceuticals to validate the accuracy of the filled prescription through an NIR spectrographic or other chemical analysis technique.

More particularly, what is needed is a system that allows the replacement of the manual verification techniques that most pharmacies rely on today, thereby allowing verification and validation steps to be performed automatically and consequently requiring less trained and less expensive supervision. What is also needed is a system that will account for the predicted added prescription throughput and reduced supply of trained pharmacists that the pharmacy industry will face in the coming years. Finally, what is needed is a system that will help reduce per prescription costs, reduce error rates in filling prescriptions, increase pharmacist productivity, reduce the time to complete a prescription order and allow pharmacists to spend more time with their customers and engaged in other professional responsibilities.

SUMMARY OF THE INVENTION

In one aspect, an apparatus for verifying the identity of a dispensed pharmaceutical comprises an analysis unit adapted to determine a property of the dispensed pharmaceutical, an input device adapted to receive predetermined identifying information corresponding to the dispensed pharmaceutical, and a comparison unit adapted to compare the determined property of the dispensed pharmaceutical with the predetermined identifying information.

In another aspect, a method of verifying a prescription, wherein the prescription comprises a pharmaceutical compound, comprises associating the prescription with a unique identifier, storing the unique identifier, determining the identity of the pharmaceutical compound, and comparing the identity of the pharmaceutical compound with the unique identifier.

In another aspect, a method of adapting an existing pharmacy information system to perform verification of a dispensed pharmaceutical comprises providing an analysis unit adapted to measure a property of the dispensed pharmaceutical, providing an input device adapted to receive predetermined identifying information corresponding to the dispensed pharmaceutical, and providing a comparison unit adapted to compare the measured property of the dispensed pharmaceutical with the predetermined identifying information.

In another aspect, A inspection system for verifying the contents of a filled prescription, comprises a spectrometer adapted to determine the spectral signature of the contents of the filled prescription, a scanner adapted to receive identifying information corresponding to the filled prescription, a data storage device coupled to the scanner and adapted to store the identifying information corresponding to the filled prescription, wherein the data storage device comprises a plurality of data items, each of the plurality of data items corresponding to a known prescription pharmaceutical spectral signature.

In another aspect, a method of filling a prescription, comprises receiving a prescription request, entering the prescription request into an information system, dispensing the prescription from a supply source into a customer container, applying an identification label on the customer container, wherein the identification label contains identifying information corresponding to the prescription, storing the identifying information corresponding to the prescription, determining the identity of the prescription, and comparing the identity of the prescription to the identifying information.

As will become apparent to those skilled in the art, numerous other embodiments and aspects will become evident hereinafter from the following descriptions and claims.

BRIEF DESCRIPTION OF THE DRAWINGS

The drawings illustrate both the design and utility of the preferred embodiments of the present invention, wherein.

DETAILED DESCRIPTION

Approximately 90% of the most commonly prescribed and dispensed solid-dosage pharmaceuticals can be identified through an NIR or other spectroscopic technique with 100% accuracy. By comparing the "chemical signature" of a dispensed or filled prescription to an electronic database of known formulations, there can be near 100% assurance that a dispensed drug is correct in both type and concentration.

Figure 1:
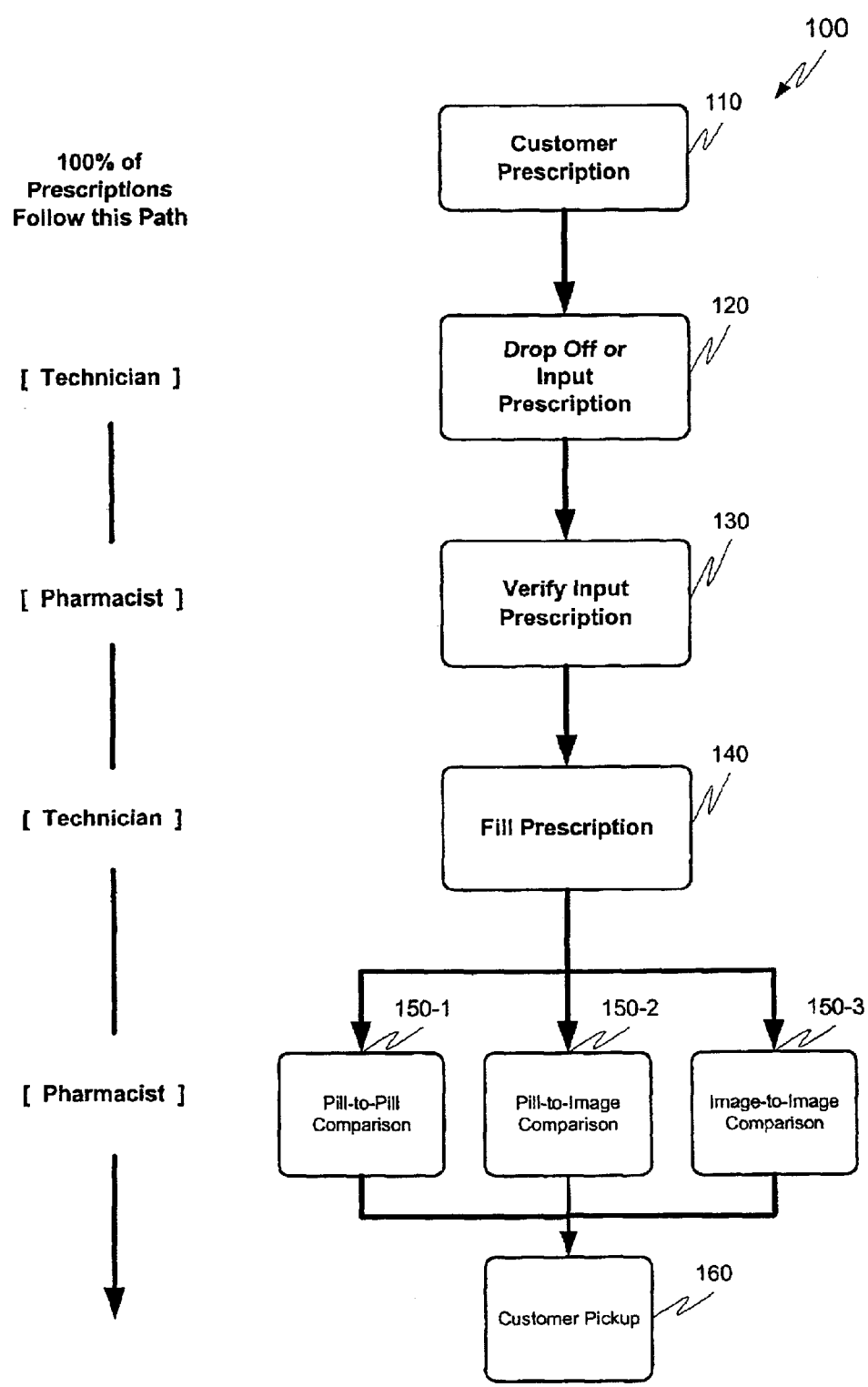
FIG. 1 is a flow chart depicting a known pharmacy filling and verification process.

FIG. 1 shows a workflow and validation process 100 that is typical for known pharmacies and their associated prescription filling procedures. While this example is based on the filling of a solid dosage prescription, similar procedures are utilized for other dosage forms. In the workflow 100 shown in FIG. 1, 100% of the drugs stocked by a pharmacy and filled for a patient follow the same path. In the flow diagram 100, the bracketed text to the left indicates the pharmacy personnel that would typically perform the corresponding task. To begin the prescription filling process, a customer drops off or calls in an order at 110. The order consists of one or more new or refill prescriptions. The prescription(s) are entered into the pharmacy's information system at 120. As indicated, step 120 is typically performed by a technician or other administrative staff, although it may be performed by a pharmacist as well. After the order has been entered into the pharmacy information system, a pharmacist verifies that the prescription has been entered into the pharmacy information system correctly at 130. Step 130 is typically performed by comparing the information entered into the pharmacy information system with the information contained on the written prescription. Some systems actually scan the written prescription into the pharmacy information systems so that a side by side comparison can be made on a computer screen of an image of the written prescription prepared by a physician and the data entered by the technician at step 120. Once the entered prescription is verified at 130, the filling process begins. A technician fills the prescription at 140. Some known systems utilize bar codes to ensure that the correct supply bottle has been selected by the technician. All manufacturer supply bottles include a bar coded identification number that contains information unique to the product and manufacturer. Other tasks that are typically performed at step 140 include assigning a tote (customer container to hold multiple prescriptions for the same customer) to the order, scanning the supply bottle, counting tablets and filling the vials, printing labels and applying the label to the vial, and closing the vial and placing it in the assigned tote. Further details of these visual pharmacy inspection and verification systems can be found in U.S. Pat. Nos. 5,597,995, 6,176,392, and 6,202,923, the details of which are hereby incorporated by reference into the present application.

After the order has been filed at 140, the pharmacist must verify the contents and accuracy of the filled order at 150. Since the pharmacist is ultimately responsible for the accuracy of the filled order, this task is usually not assigned to a technician or other clerical employee. While the verification step 150 can be performed in several different ways, all existing pharmacy systems utilize a visual verification process that is carried out by a professional pharmacist. FIG. 1 includes several examples (150-1, 150-2, and 150-3) of how this visual verification process is normally handled.

At 150-1 a pharmacist compares the contents of the filled customer vial with the supply bottle that was used to fill the prescription. In the case of 150-1, the supply bottle is often left in the customer tote with the filled vial for the pharmacist to use in verifying the vial's contents. This is, in effect, a tablet-to-tablet comparison. Alternately, at 150-2 the pharmacist compares the contents of the filled vial to an image of the prescribed drug that is retrieved from a database displayed on a computer monitor for the pharmacist to view. This is a tablet-to-image comparison. Alternately, at 150-3 the pharmacist compares an electronic image taken of the filled vials with a database image of the same prescribed drug. This is an image-to-image comparison. Certain automated prescription filling systems utilize these image-based verification schemes by taking an image of the filled vial before it is released to the pharmacist for verification. Finally, at 160 the order is placed with the appropriate paperwork in a pickup area for the customer to receive the prescription.

As explained above, these known pharmacy systems all suffer from the same general problems in that they rely on a visual verification performed by a human operator to validate that the prescription has been properly filled. The result is that a significant number of prescriptions are incorrectly filled. Additionally, the pharmacist, who is ultimately responsible for the accuracy of the filled prescription, spends a significant portion of his or her day performing these verifications. These and other known pharmacy inspection systems are more fully described in U.S. Pat. Nos. 5,597,995, 6,176,392, and 6,202,923, the details of which have previously been incorporated by reference into the present application.

In accordance with an aspect of the present invention, an inspection system is provided that preferably replaces the visual verification steps associated with traditional and known pharmacy systems. Alternatively, an inspection system constructed in accordance with the present invention can augment existing visual verification systems. In addition, an inspection system constructed in accordance with the present invention can preferably be adapted for use with an existing pharmacy information system, or can be utilized as a stand alone and portable unit.

Figure 2:
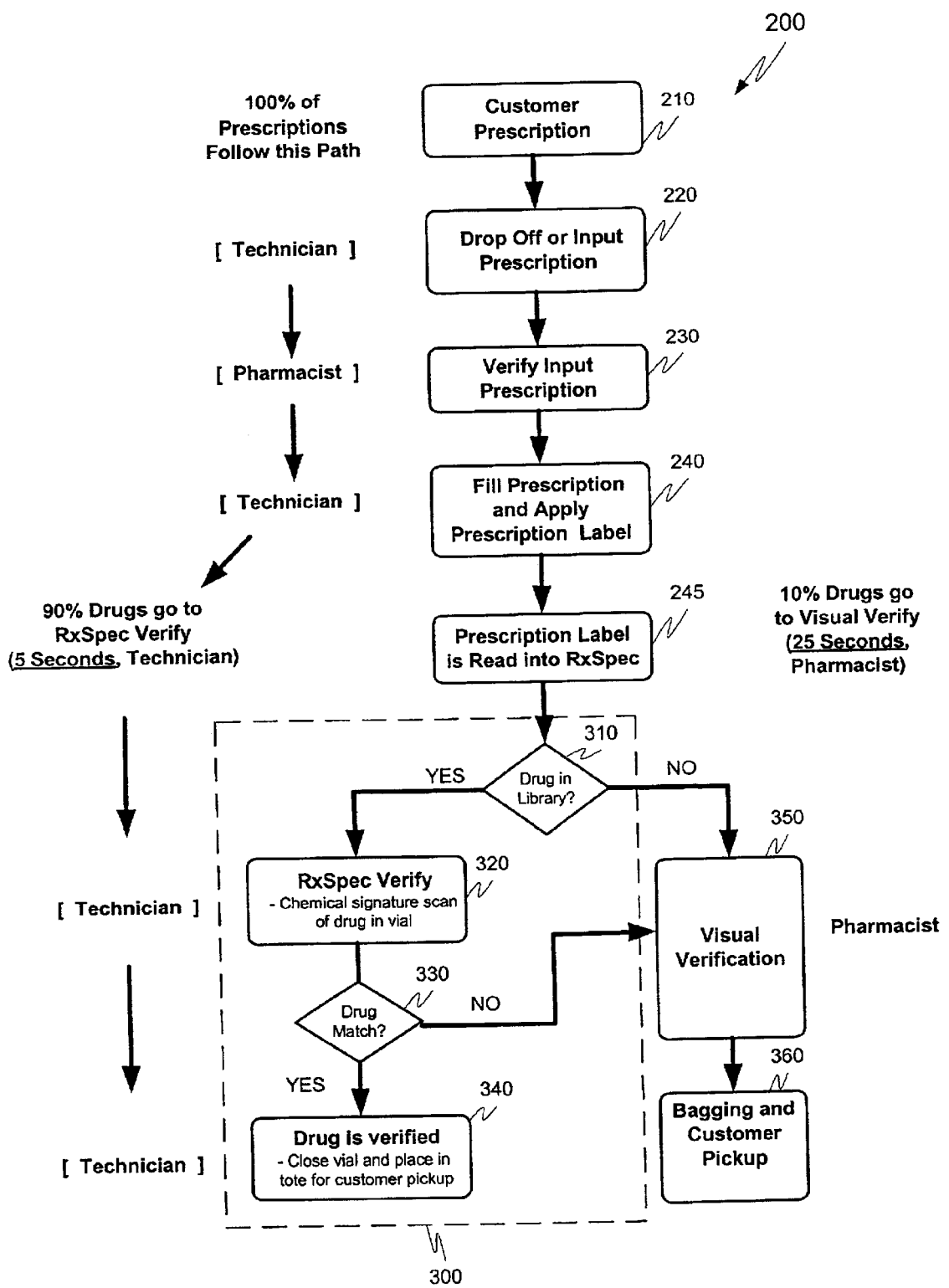
FIG. 2 is a flow chart showing a pharmacy filling and verification process in accordance with an aspect of the present invention.

FIG. 2 illustrates a work flow 200 associated with one aspect of a pharmacy inspection and validation system constructed in accordance with the present invention. While this example is based on the filling of a solid dosage prescription, similar procedures may be utilized for other dosage forms. A customer drops off or otherwise communicates a prescription to the pharmacy at 210. At 220, the customer's prescription is input into the pharmacy's information system or, if the prescription is for a refill, the prescription is recalled from the pharmacy's information system. Step 220, as in the system of FIG. 1, is typically performed by a pharmacy technician, rather than by a licensed pharmacist. At 230, a pharmacist performs a verification that the customer prescription is properly entered into the pharmacy information system. Step 230 is typically performed by comparing the information entered into the pharmacy information system with the information contained on the written prescription. As in the system of FIG. 1, some systems actually scan the written prescription into the pharmacy information system so that a side by side comparison can be made on a computer screen of an image of the written prescription prepared by a physician and the data entered by the technician at step 220. At 240, after the entered prescription is verified by the pharmacist, it is released for filling (typically done by a technician). The technician then fills the customer vial and applies the prescription label, including a bar code linked to both the prescription number and the dispensed drug's unique NDC code, to the vial. Preferably, the bar code on the prescription label includes a prescription number that is unique to that specific prescription fill. For example, a refill prescription will get a new prescription number and not one identical to the original prescription. This accounts for the situation where two prescriptions for the same drug are being filled at the same time and allows a unique identifier to be associated with the prescription in addition to the manufacturer's NDC code.

At this point, the filled vial is inserted into a chemical analysis system. The chemical analysis and validation system is referred to herein as the RxSpec™ system. At 245, the bar code label on the filled customer prescription vial is read into the RxSpec™ system. The steps performed by the RxSpec™ system, and in general, the pharmacy chemical analysis and validation system, are generally shown in FIG. 2 within the dashed lines represented by reference number 300. Preferably, the RxSpec™ system utilizes visible (Vis) and near-infrared (NIR) spectroscopy to analyze and identify the contents of the filled prescription vial, however, it is contemplated that any number of other methods or variations of NIR spectroscopy can be utilized in a pharmacy system constructed in accordance with the present invention. For example, various forms of optical spectroscopy, ultraviolet & visible (UV-Vis), Ultra-violet/visible/near infrared (UV-Vis-NIR), infrared, or Raman spectroscopy may be utilized in a chemical analysis and verification system constructed in accordance with the present invention. Additionally, optical imaging technology can also be integrated into a chemical analysis and verification system constructed in accordance with the present invention, such as systems that are adapted to perform optical character recognition (OCR), color analysis, or other physical (rather than chemical) property analysis and identification.

At 310, the RxSpec™ system compares the NDC derived from the bar code scanned from the label on the customer prescription vial, to a database of drugs that the RxSpec™ has been formatted or otherwise calibrated to chemically identify. At this point, no chemical identification has taken place, rather the RxSpec™ system is comparing the name and dosage of the drug associated with the customer's prescription with a preloaded database of drugs that the RxSpec™ system has been calibrated to analyze. The database also contains a representation of the unique chemical signatures associated with each of these calibrated drugs. It is contemplated that this database of calibrated drugs will be periodically updated to reflect new drugs that come on the market as well as existing drugs that are calibrated to be recognized by the RxSpec™ system. If the customer's prescription is contained in the RxSpec™ database, then, at 320, the RxSpec™ system performs a chemical identification on the actual tablets, or capsules that are contained in the customer's prescription vial. At 320 the RxSpec™ system scans the items in the filled vial and measures the chemical signature of the items. This actual chemical signature is then matched to a particular drug and dosage level from the database of calibrated drugs. This information is then compared at 330 to the prescription information taken from the bar code label on the customer's filled prescription vial, which has been previously stored by the RxSpec™ system. If the results from the RxSpec™ system match the information from the bar code on the customer's filled prescription vial, the RxSpec™ system signals that the filled prescription has been verified and the technician then closes the filled vial, finalizes the prescription, and places it into a tote for customer pickup at 340. The inspection and validation steps associated with the RxSpec™ system are automatic and can therefore be easily performed by a technician rather than a pharmacist.

If at step 310 it is determined that the customer's prescription is not contained in the RxSpec™ database, and therefore not amenable to chemical verification, the RxSpec™ system signals the technician that it can not chemically verify the customer's prescription and that another form of verification is necessary. At 350, an alternate verification means is then employed, such as one of the visual verification techniques previously described in connection with FIG. 1. After the customer's filled prescription has been verified the prescription is finalized, bagged, and placed in a tote for customer pickup at 360.

From experimental results, it has been determined that in the process flow of FIG. 2, approximately 90% of the drugs will be able to be recognized by the RxSpec™ system and will therefore be able to be automatically verified and validated by chemical analysis and comparison to the prescription's bar code information. Those drugs that are not recognized by the RxSpec™ system will need to be visually verified as described above or by a similar method. In practice, verifying a prescription using the RxSpec™ system is approximately 5 times faster than using a manual verification method, such as visual verification. For example, in efficiently run pharmacies, it takes approximately 25 seconds to visually verify a prescription. Using the RxSpec™ system has been demonstrated to take approximately 5 seconds. Furthermore, the RxSpec™ system can be run by a technician since the verification process is entirely automatic. Visual verifications, since they are subject to user error, are typically performed by a pharmacist. Large retail pharmacies filling as many as 300 prescription per day and utilizing a verification system constructed in accordance with the present invention will realize a net result of the pharmacist having approximately 1.7 hours of available time to perform other tasks such as patient consultation or filling additional prescriptions. The RxSpec™ system directly identifies the actual drug contained in the prescription vial and compares it to a pre-stored library of drug signature data. For those drugs that are recognized by the RxSpec™ system, this verification is accomplished with virtually 100% accuracy. Other benefits are also realized by implementing the inspection and validation process of FIG. 2. For instance, pharmacist job satisfaction and morale will likely increase as a result of reduced stress and less time performing visual verification tasks; there will be faster prescription throughput time for those drugs verified by the RxSpec™ system; there is a reduction in overtime wages; and the use of such an automated verification systems may be recognized as evidence of proper prescription filling in the context of litigation.

Figure 3:
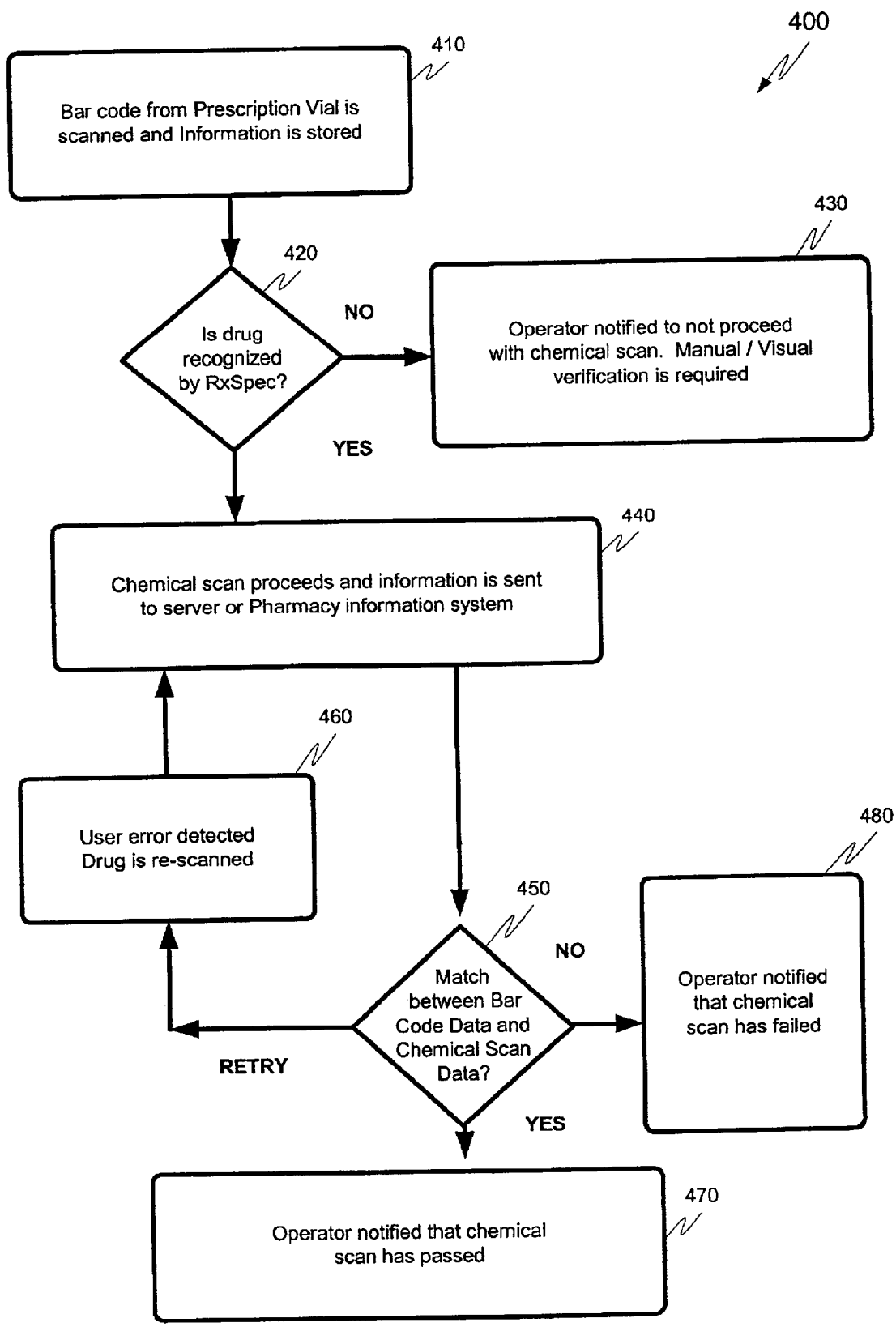
FIG. 3 is a detailed flow chart of the chemical verification process in accordance with an aspect of the present invention.

FIG. 3 shows a detailed flow diagram 400 of a portion of the RxSpec™ system, and more particularly, one embodiment of the automated chemical identification and verification process. At 410, a technician scans the bar code on a prescription vial's label using a scanner attached to the RxSpec™ system. Preferably, the scanner presents an audible tone or visual indicator letting the user know that the label has been scanned successfully. The data obtained from the bar code is sent to and stored on a data storage device such as a magnetic disk drive or a network server. It is contemplated that various computer hardware platforms may be utilized in such a system such as PCDOS, WINDOWS, UNIX, LINUX, etc. Additionally, the hardware platform may be part of the pharmacy's existing information system.

After the data from the bar code label has been stored, the RxSpec™ system determines at 420 whether the drug, as represented by the data from the scanned bar code label on the customer's prescription vial, is in the RxSpec™ data library, and thus recognized by the RxSpec™ system. The RxSpec™ data library, is preferably a stored database of drug formulations, dosage signatures, and their associated product names, manufacturers and other identifying information that is recognized by and calibrated to the RxSpec™ system. If the drug in the filled prescription vial is not recognized by the RxSpec™ system, then at 430, the data server sends a message to the RxSpec™ system and the technician is notified not to proceed with a chemical scan of the filled prescription through the RxSpec™ system. The technician and the general pharmacy information system are notified that this particular drug must follow a standard manual/visual verification routine as previously described in conjunction with FIG. 1.

If the drug in the filled prescription vial is recognized by the RxSpec™ system, then at 440, the RxSpec™ system indicates to the technician that he can proceed with the chemical scan. The technician then places the filled prescription vial into the RxSpec™ system, the drug, while still in the prescription vial, is scanned and the resulting chemical signature data is sent to the server or existing pharmacy information system. At 450, the RxSpec™ system compares the data obtained from the prescription vial bar code to the data obtained from the chemical scan and determines whether there is a match or whether there is some form of user error such as the prescription vial being improperly aligned in the RxSpec™ system. If there is a user error detected, the RxSpec™ system alerts the technician at 460 and allows the technician to rescan the drug. If the RxSpec™ system determines that the chemical scan of the drug and the data from the prescription vial bar code are a match, the RxSpec™ system at 470 sends a message to the technician that the drug has passed the chemical inspection and validation and that the prescription vial can be capped and the prescription completed. In this case, visual inspection is not necessary, although, if desired, the pharmacist can choose to also visually verify the filled prescription. If the RxSpec™ system determines that the chemical scan of the drug and the data from the prescription vial bar code are not a match, the RxSpec™ system at 480 sends a message to the technician that the drug has failed the chemical inspection and validation process. A further message may also be sent to the technician indicating that either visual verification must be completed or that the pharmacist must otherwise intervene in the prescription filling process.

Figure 4:
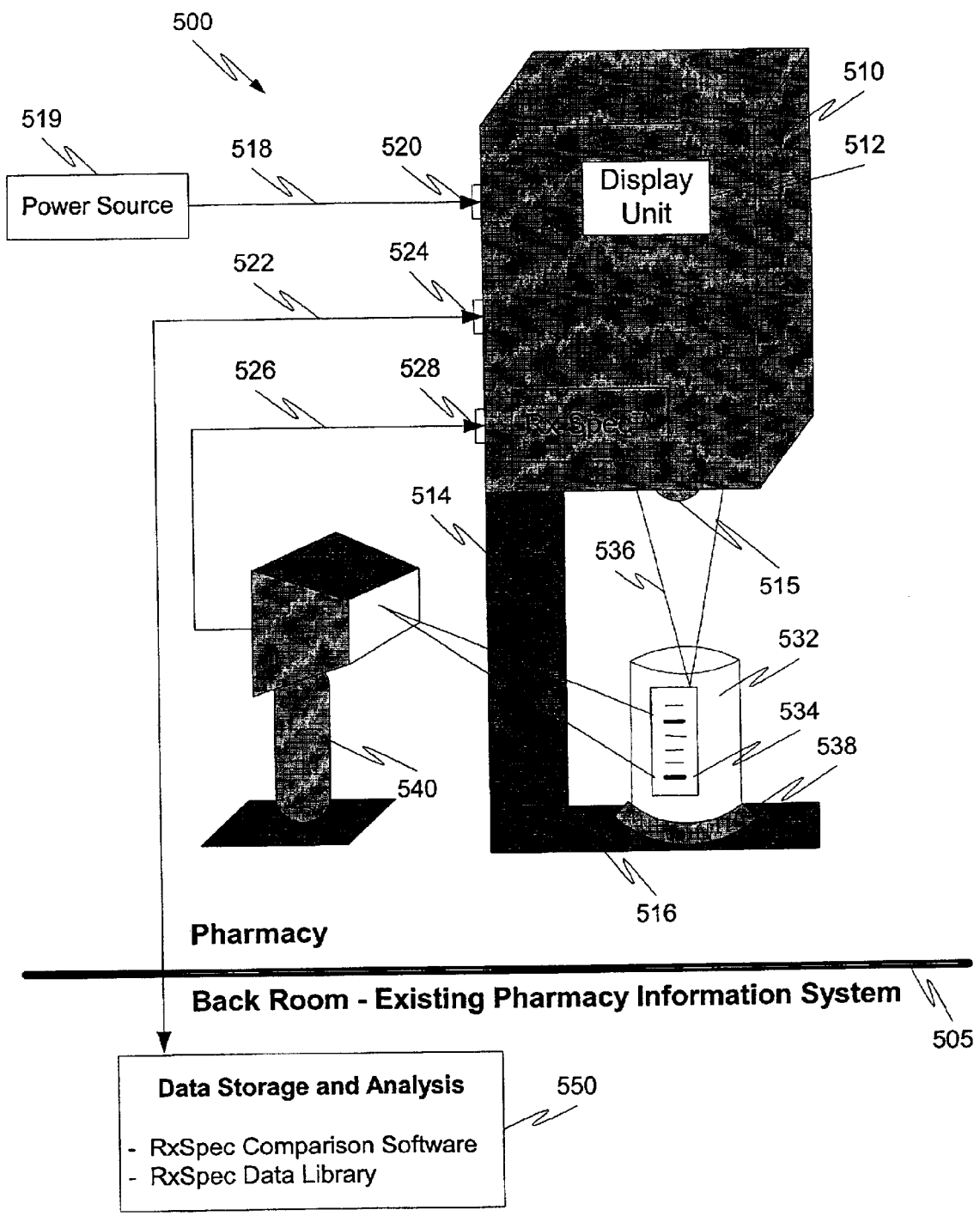
FIG. 4 is an embodiment of a chemical analysis and verification system in accordance with an aspect of the present invention.

FIG. 4 shows one embodiment of an RxSpec™ system 500 constructed in accordance with an aspect of the present invention. The RxSpec™ system 500 can be formatted to function either as a stand alone unit or to integrate into an existing pharmacy information system. Line 505 in FIG. 4 defines an example of how the stand alone portion of the RxSpec™ system could be incorporated into an existing pharmacy information system. The portion above the line 505 would be located in the actual pharmacy within easy access of the pharmacist, while the portion below line 505 represents an existing pharmacy information system such as a network server or other information system platform. As a stand alone unit, the RxSpec™ system would preferably be linked to a PC based computer or portable computer system.

The RxSpec™ system 500 includes a main housing unit 510 that contains the chemical analysis hardware and associated electronics. Preferably, the chemical analysis hardware is an Vis-NIR-based spectrometer system adapted for use in the RxSpec™ system. However, other chemical analysis systems are contemplated by the present invention such as various forms of optical spectroscopy, ultra-violet & visible (UV-Vis), Ultra-violet/visible/near infrared (UV-Vis-NIR), infrared, or Raman spectroscopy. It is also envisioned that digital imagery could be used to automatically derive information on the size, shape, and color of solid dosage forms. The main housing 510 includes a local display unit 512 that provides a user with information such as pass/fail results, system status, power availability, and various other functional indicators of the RxSpec™ system 500. The main housing 510 is positioned on a mounting bracket 514 so that an imaging aperture or entrance slit 515 of the main housing faces a sample plate 516. The sample plate 516 is adapted to receive a sample, such as a prescription vial 532, so that the imaging aperture 515 substantially aligns with the vial 534. Preferably a guide 538 is incorporated into the sample plate 516 to easily and consistently align the vial 532 under the imaging aperture 515.

The main housing 510 is connected to a power source 519 through a cable 518 and connector 520. The main housing 510 of the RxSpec™ system preferably receives data through two separate connections. First, the main housing 510 receives data from data storage and analysis unit 550 through cable 522 and connector 524. Second, the main housing 510 receives data from scanner 540 through cable 526 and connector 528. The data storage and analysis unit, can, as described above, be either a network based system connected to the main housing 510 through a 10/100 BaseT Ethernet connection, or it can be a local system, such as a PC or laptop computer connected through a serial or USB port. Various other connection schemes are also contemplated.

In operation, data obtained through the scanner 540 from a label 534 applied to the vial 532 is compared to data obtained by chemically identifying the actual product contained in the vial 532. Preferably the label 534 is a bar code containing the unique prescription number. In one embodiment a spectrometer-based system shines a light beam 536 at the product in the vial 532 and acquires the chemical signature data of the product. The chemical signature data and the data obtained from the bar code label 534 are both sent back to the data storage and analysis unit 550. The data storage and analysis unit 550 first queries the prescription database to determine the NDC of the drug used to fill the prescription currently being verified. The data storage and analysis unit 550 preferably contains a database of chemical fingerprints corresponding to the drugs available in the pharmacy. The database also includes the corresponding NDC, manufacture name, drug name, and other identifying information about the available drugs. The data storage and analysis unit 550 is also adapted to run comparison software and other algorithms that automatically compare the NDC determined from the bar code label 534 and the signature of the analyzed product 534 contained in the vial 532. A message is sent from the data storage and analysis unit 550 back to the RxSpec™ system's main housing 510 alerting the user whether the prescription being verified has passed or failed the verification process.

The data storage and analysis unit 550 can take various forms as briefly described above. First, it can be part of an existing pharmacy information system, such as a UNIX based server where the RxSpec™ signature library and comparison software reside on a storage area within the existing server unit. Second, the data storage and analysis unit 550 can be a stand alone computer unit such as a PC based system or laptop computer system. In this case, the RxSpec™ chemical signature library and comparison software reside on a storage area within the stand alone unit. In that regard, the RxSpec™ system would be more conducive to portability and could be utilized in other sites than just pharmacies such as emergency rooms and ambulance environments.

Figure 5:
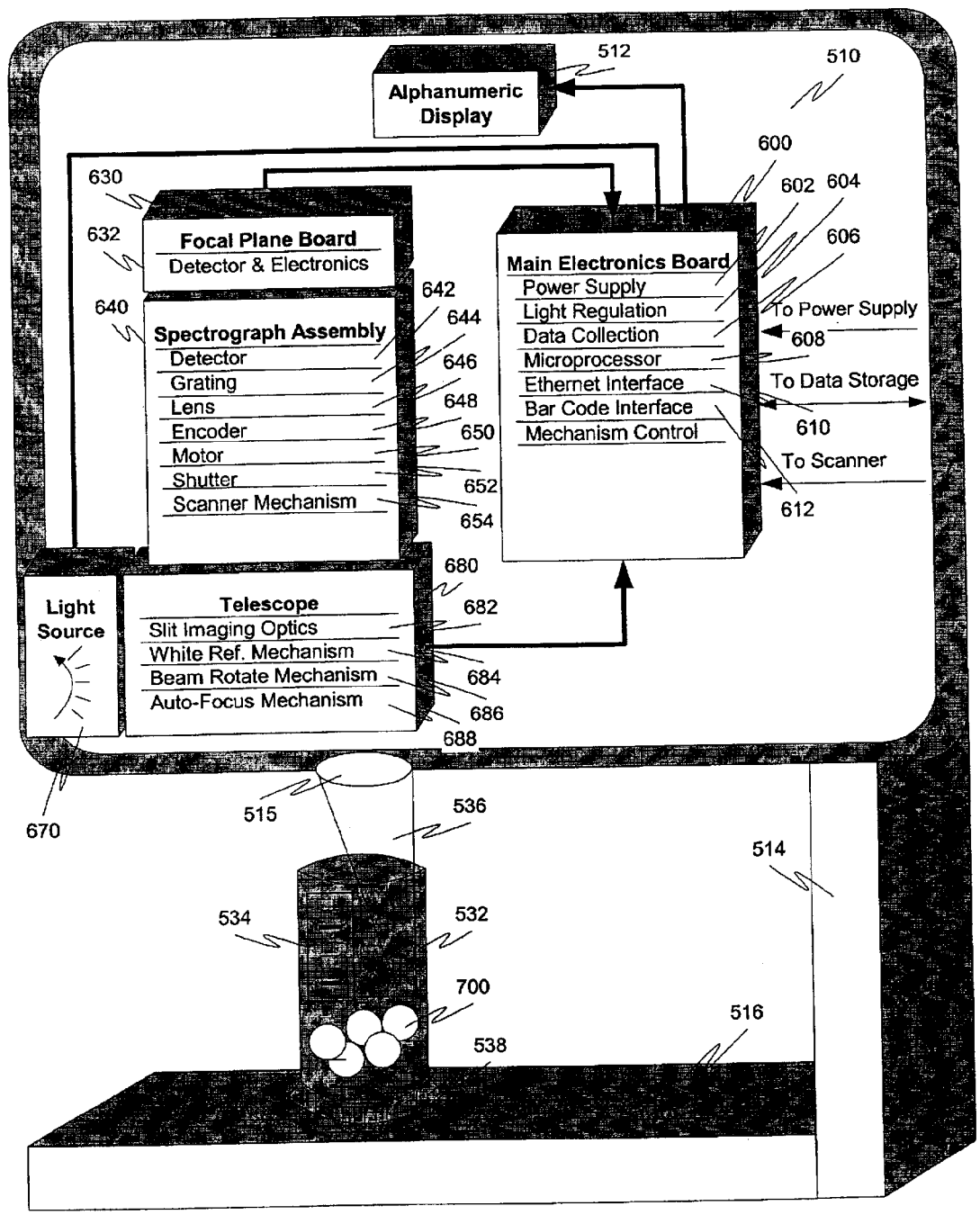
FIG. 5 is a detailed diagram of the main housing of a chemical analysis and verification system in accordance with an aspect of the present invention.

FIG. 5 shows a schematic detail of the housing 510 and, more particularly, one embodiment of its internal construction and interrelation between its various components. The housing 510 as shown in FIG. 5, is configured for use with a spectrometer based analysis system, and more particularly, a Vis-NIR spectrometer system, however, it is contemplated that other types of non-invasive chemical and/or physical analysis systems can be incorporated into systems constructed in accordance with the present invention and as described above. The housing 510 generally contains six main components or modules. An alphanumeric display 512, a main electronics board 600, a focal plane board 630, a spectrograph assembly 640, a light source 670 and a telescope 680. The arrows in FIG. 5 show one embodiment of the inter-relationship between the different components of the main housing 510.

The alphanumeric display 510 is adapted to display a number of different information parameters pertaining to the status of the RxSpec™ system such as power on status, pass or fail results of an ongoing chemical screen or identification, etc. The main electronics board 600 includes the following modules and functions: a power supply 602, light regulation 604, data collection 606, microprocessor 608, ethernet interface 610, scanner or bar code interface 612, and a mechanism control 614. The main electronics board 600 also preferably includes the connection ports for the power supply, the ethernet connection and a serial port for the scanner interface.

The focal plane board 630 includes the spectrometer detector and associated electronics 632. The detector 632 interprets the reflected light data from a sample being analyzed and transmits it back to the main electronics board for interpretation. The detector and electronics 632 can be one of many known in the spectroscopy art. In other embodiments, the focal plane board may include an exit and entrance slit for the spectrometer, a cut-on filter, a light source mirror, and mounts for each of the slits and filter.

The spectrograph assembly 640 includes a detector 642, grating 644, lens 646, encoder 648, motor 650, shutter 652, and scanner mechanism 654. The light source 670 is preferably a white light that provides a broad range of wavelengths and is adapted to illuminate a sample 700 that is being analyzed. The light source 670 may be integrated with the telescope assembly 680. The telescope assembly 680 includes slit imaging optics 682, a white reference mechanism 684, a beam rotate mechanism 686, and an auto-focus mechanism 688.

Figure 6:
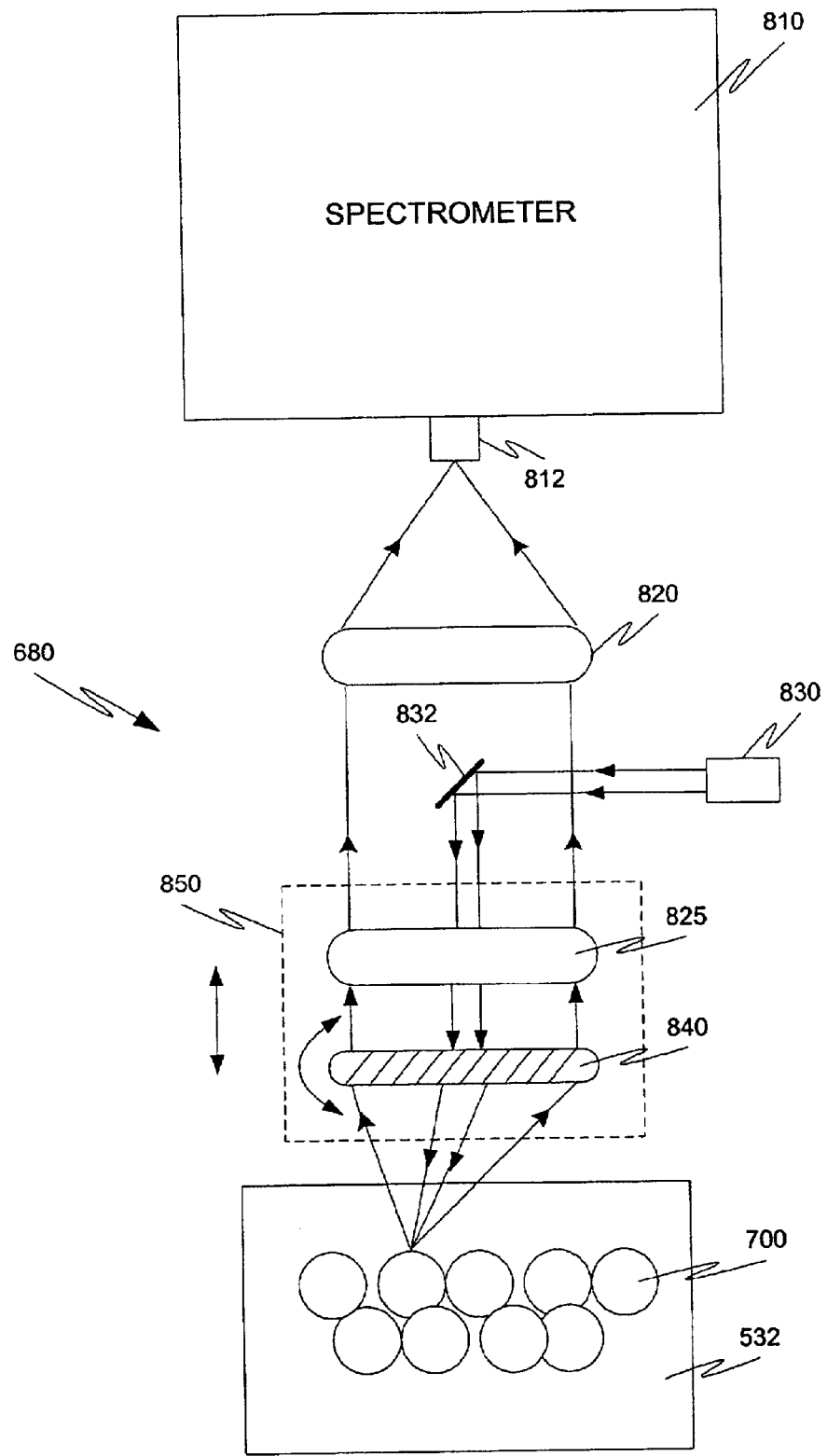
FIG. 6 is a detailed diagram of the spectrometer and telescope assembly of a chemical analysis and verification system in accordance with an aspect of the present invention.

FIG. 6 shows one embodiment of elements from the spectrograph assembly 640 and telescope 680 from FIG. 5, and more particularly, the relationship between the telescope and focusing elements to the spectrometer. It is contemplated that numerous other embodiments of the spectrometer and telescope can be incorporated into a pharmacy inspection system in accordance with the present invention, many of which are known to those of skill in the art of spectroscopy and chemical analysis. In FIG. 6, the combined spectrometer and telescope assembly includes a spectrometer 810 having an entrance slit 812, a pair of lenses 820 and 825, a collimated light source 830 a mirror 832, and a rotating beam steering element 840. The telescope assembly is generally referred to as 680. The dashed line 850 represents those elements of the telescope assembly that are adapted to move up and down in order to adjust the focal point of the system. Correct focus of the system is obtained by automatically adjusting the position of the telescope focusing elements 850 to a position that provides the maximum signal as measured by the spectrometer 810. The product being inspected 700 sits in the vial 532 and is positioned under the telescope assembly 680. The rotating beam steering element 840 is adapted to take a series of measurements of the product 700. Preferably, the measurements are collected in a circular or ring shaped pattern to ensure consistency of the contents of the vial.

Figure 7:
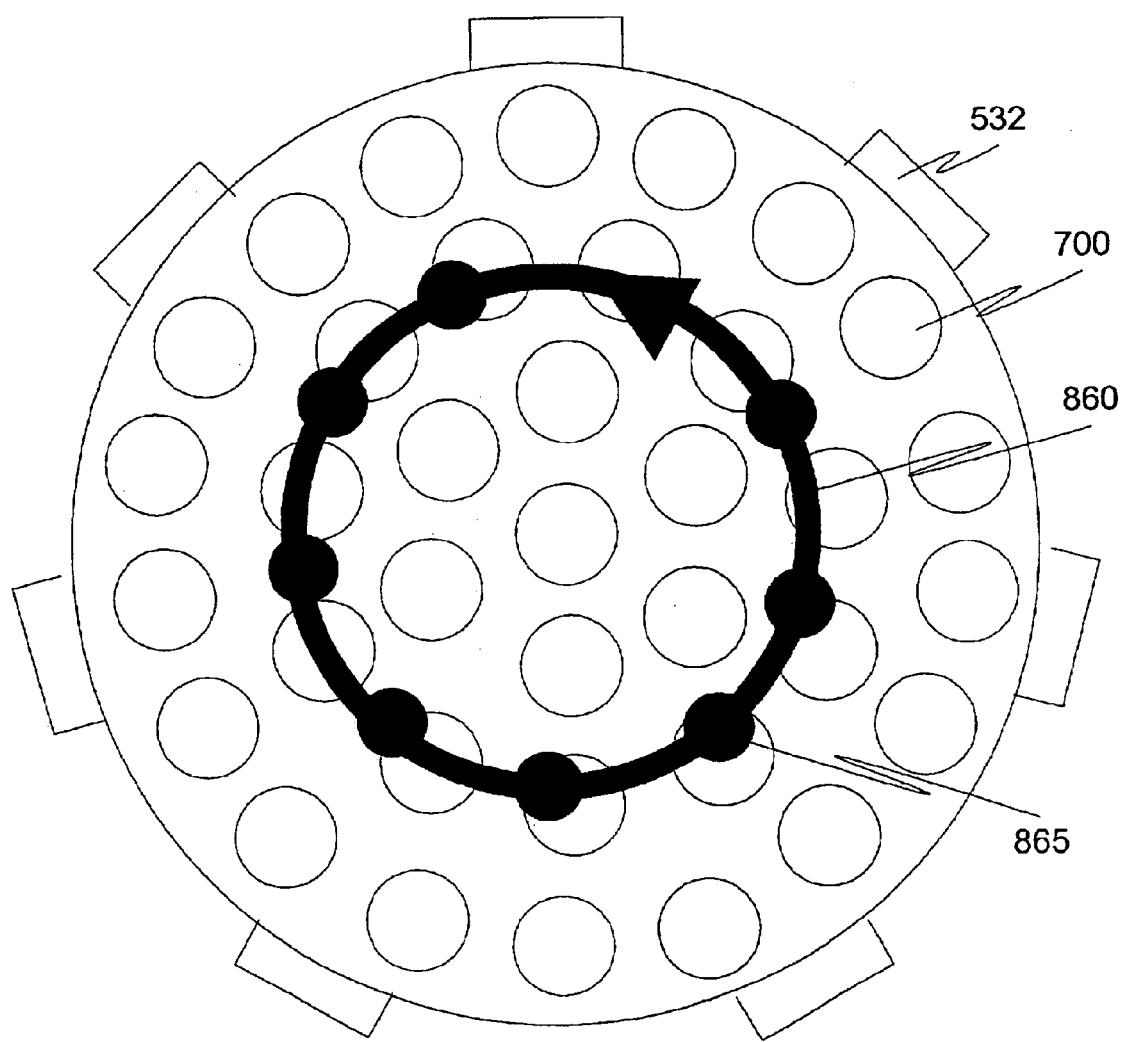
FIG. 7 is a top view of a filled prescription vial as it is seen by a chemical analysis and verification system in accordance with an aspect of the present invention.

FIG. 7 shows an image of the vial 532 filled with a product 700 that is being inspected. The image in FIG. 7 is how the vial 532 and product 700 would appear to the telescope assembly, i.e. looking down into the filled vial. Ring 860 represents the scanning path produced by the rotating beam steering element 840 and points 865 represent a series of locations measured by the RxSpec™. Other sampling patterns or analysis algorithms may be incorporated into the spectrometer system in accordance with the present invention.

Although the present invention has been described and illustrated in the above description and drawings, it is understood that this description is by example only and that numerous changes and modifications can be made by those skilled in the art without departing from the true spirit and scope of the invention. The invention, therefore, is not to be restricted, except by the following claims and their equivalents.

What is claimed is:

1. A method of verifying a prescription, wherein the prescription comprises a pharmaceutical compound, the method comprising:
   associating the prescription with a unique identifier;
   storing the unique identifier;
   determining the identity of the pharmaceutical compound; and
   comparing the identity of the pharmaceutical compound with the unique identifier.

2. The method of claim 1, further comprising:
   associating the identity of the pharmaceutical compound with a unique chemical signature;
   determining whether the chemical signature corresponds to the unique identifier;
   displaying a first signal if the chemical signature corresponds to the unique identifier; and
   displaying a second signal if the chemical signature does not correspond to the unique identifier.

3. The method of claim 1, wherein associating the prescription with a unique identifier comprises:
   receiving the unique identifier from a pharmacy information system, wherein the unique identifier is in the form of a bar code; and
   associating the bar code with the prescription.

4. The method of claim 3, wherein storing the unique identifier comprises reading the bar code with a hand-held scanner.

5. The method of claim 1, wherein the unique identifier includes the manufacturer of the prescription pharmaceutical.

6. The method of claim 1, wherein the unique identifier includes the name and dosage level of the prescription pharmaceutical.

7. A inspection system for verifying the contents of a filled prescription, comprising:
   a spectrometer adapted to determine the spectral signature of the contents of the filled prescription;
   a scanner adapted to receive identifying information corresponding to the filled prescription;
   a data storage device coupled to the scanner and adapted to store the identifying information corresponding to the filled prescription;
   wherein the data storage device comprises a plurality of data items, each of the plurality of data items corresponding to a known prescription pharmaceutical spectral signature.

8. The inspection system of claim 7, wherein the spectrometer operates in the ultra-violet, visible, and near infrared wavelengths.

9. The inspection system of claim 7, further comprising a telescope assembly coupled to the spectrometer.

10. The inspection system of claim 7, wherein the spectrometer is operative to focus the telescope assembly.

11. The inspection system of claim 7, wherein the telescope is adapted for confocal viewing and illumination.

12. The inspection system of claim 7, wherein the telescope further comprises a rotating beam steering element adapted to obtain multiple readings.

* * * * *